(12) United States Patent  
Wieder et al.

(10) Patent No.: US 8,594,760 B2  
(45) Date of Patent: Nov. 26, 2013

(54) IN VIVO ANALYTE MONITOR WITH MALFUNCTION DETECTION

(75) Inventors: Herbert Wieder, Mannheim (DE); Michael Marquant, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1179 days.

(21) Appl. No.: 12/201,649

(22) Filed: Aug. 29, 2008

(65) Prior Publication Data

US 2009/0057148 A1  Mar. 5, 2009

(30) Foreign Application Priority Data

Sep. 1, 2007 (EP) .................................... 07017172

(51) Int. Cl.  
*A61B 5/05* (2006.01)

(52) U.S. Cl.  
USPC ........................................................ 600/345

(58) Field of Classification Search  
None  
See application file for complete search history.

(56) References Cited

U.S. PATENT DOCUMENTS 5,372,133 A  12/1994  Esch  
2007/0163894 A1*  7/2007  Wang et al. .................... 205/792

FOREIGN PATENT DOCUMENTS

EP  0161673 B1  11/1985  
EP  0554955 A1  8/1993

OTHER PUBLICATIONS

Greef, Robert, "Instruments for use in electrode process research", Journal of Physics E: Sci. Instrum., vol. 11, pp. 1-12, (1978). XP009026764.

* cited by examiner

*Primary Examiner* — Brian J Gangle  
(74) *Attorney, Agent, or Firm* — Bose McKinney & Evans LLP

(57) ABSTRACT

The measuring system for in vivo monitoring of an analyte concentration with malfunction detection, comprises an electrode system, a potentiostat and an evaluation unit. The electrode system has a working electrode, a reference electrode, and a counter electrode. The potentiostat is for adjusting a difference of potential between the electric potential of the working electrode and the electric potential of the reference electrode to a specified value and for measuring an electric current flowing between the working electrode and the counter electrode. The potentiostat comprises a working electrode terminal for connection to the working electrode, a reference electrode terminal for connection to the reference electrode, and a counter electrode terminal for connection to the counter electrode. The evaluation unit monitors the electric potential of the counter electrode and generates a malfunction signal when said potential is outside a specified reference range. A method of operation is also disclosed.

13 Claims, 1 Drawing Sheet

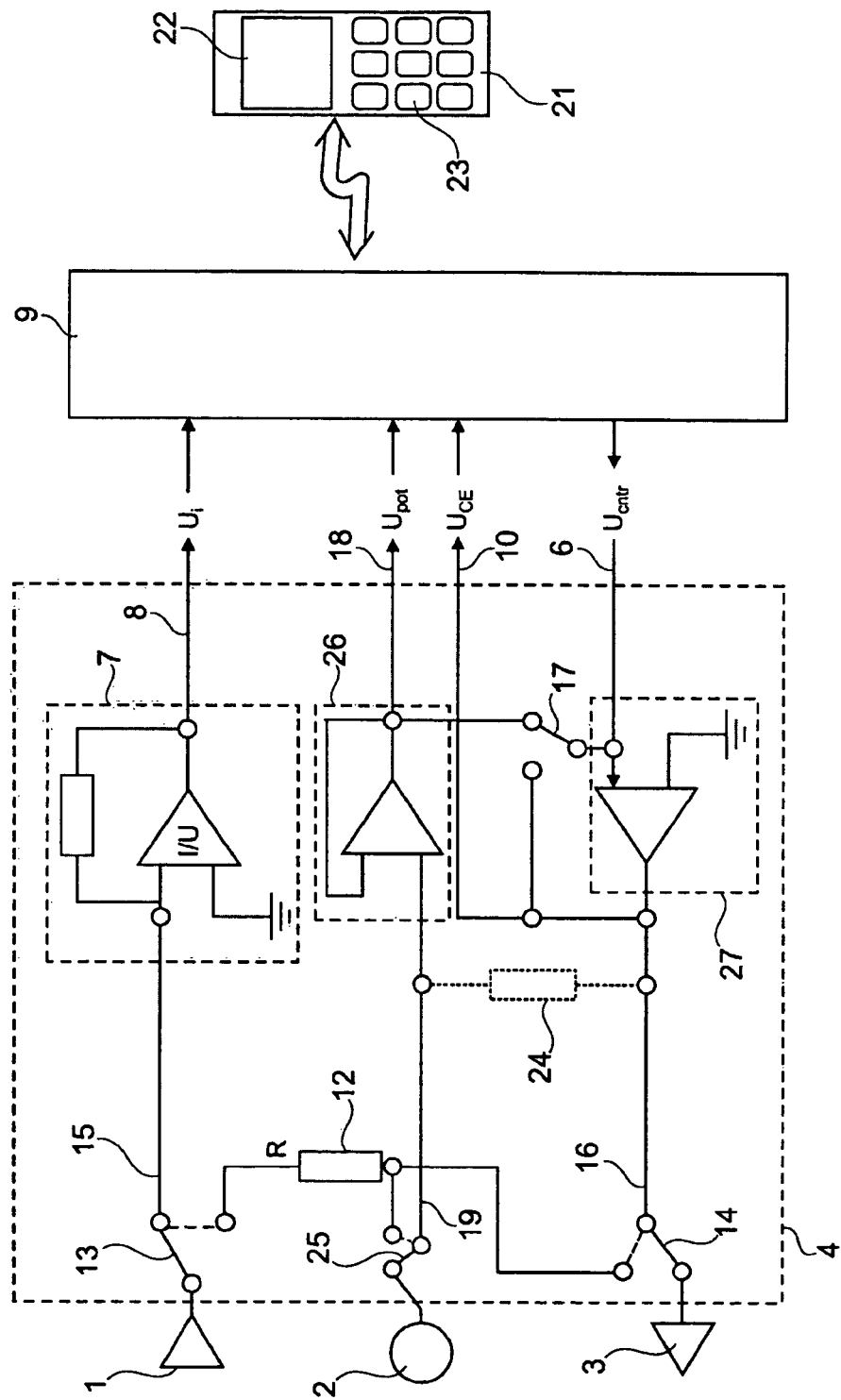

IN VIVO ANALYTE MONITOR WITH MALFUNCTION DETECTION

REFERENCE

This application is claims priority to European Patent Application No. EP 07 017 172.3 filed Sep. 1, 2008, which is hereby incorporated by reference.

FIELD

The present teachings relate to a measuring system for in vivo monitoring of an analyte concentration. Such a measuring system comprises, as a first part, an electrode system that is implanted or inserted into a patient's body for carrying out such measurements. The electrode system comprises a working electrode, a reference electrode and a counter electrode. As a second part, the measuring system has a potentiostat for setting the difference of potential between the working electrode and the reference electrode to a predefined value and for detecting the current flow between the working electrode and the counter electrode. The analyte concentration to be measured can then be derived from the intensity of that current.

BACKGROUND

Implantable or insertable electrode systems allow physiologically important analytes, such as glucose or lactate, to be measured in a patient's body. Compared with processes where a sample of a body liquid is taken and is analyzed outside the body, such in vivo measurements provide a number of essential advantages, including especially the possibility to acquire measured values automatically and continuously.

In spite of those advantages measuring systems for in vivo monitoring of analyte concentrations have not been generally accepted in the market to this day, especially for portable applications such as the "home monitoring" application, where patients monitor their blood sugar level or some other analyte concentration outside of a hospital. This is due not least to the fact that the known portable measuring systems allow measurements of analyte concentration values over a time of several days, with the precision and reliability required for medical applications, only in exceptional cases.

SUMMARY

The measuring system for in vivo monitoring of an analyte concentration with malfunction detection, comprises an electrode system, a potentiostat and an evaluation unit. The electrode system has a working electrode, a reference electrode, and a counter electrode. The potentiostat is for adjusting a difference of potential between the electric potential of the working electrode and the electric potential of the reference electrode to a specified value and for measuring an electric current flowing between the working, electrode and the counter electrode. The potentiostat comprises a working electrode terminal for connection to the working electrode, a reference electrode terminal for connection to the reference electrode, and a counter electrode terminal for connection to the counter electrode. The evaluation unit which monitors the electric potential of the counter electrode and which generates a malfunction signal when said potential is outside a specified reference range. A method of operation is also disclosed.

According to the disclosure, the electric potential of the counter electrode is monitored for detecting malfunctions of the measuring system. Using that potential a possible malfunction of the measuring system can be discovered, and a malfunction signal can be generated rapidly by an evaluation unit. The malfunction signal may be used, for example, to warn a user of the malfunction by a warning signal. Or the malfunction signal can be processed by the system internally, and the user may get knowledge of such a signal only indirectly, if at all. For example, the measuring system may be switched off transitorily as a reaction to the malfunction signal. In addition measurements generated during the time the malfunction persisted may be classified as non-reliable measurements in response to a malfunction signal so that an evaluation will not be falsified by data obtained during the time a malfunction of the measuring system persisted.

In a measuring system according to embodiments of the invention, an evaluation unit will generate a malfunction signal when the electric potential of the counter electrode is found to lie outside the limits of a predefined reference range. The electric potential of the counter electrode can be measured relative to the working electrode. However, there is also the possibility to measure the electric potential of the counter electrode relative to a different reference potential, and to specify the reference range accordingly.

The reference range of the electric potential of the counter electrode defines a range of values within which the expected values of the potential of the counter electrode relative to the reference potential or mass potential will lie during trouble-free operation. If any values of the electric potential of the counter electrode are found to lie outside the reference range, this is an indication of a malfunction.

The reference range may be firmly defined for a given electrode system. The reference range, i.e. its limits, can be defined as a function of the current flow between the working electrode and the counter electrode. The limits of the reference range then can be calculated by the evaluation unit based on a predefined formula, or can be taken from a pre-stored table. The corresponding data may be made available to the evaluation unit on a storage medium which may be delivered together with the electrodes and which may also contain calibration data regarding the measuring sensitivity, for example.

According to another possibility, the reference range, or more specifically its limits, can be defined as a function of a former-value of the electric voltage between the working electrode and the counter electrode. This is so because rapid variations of the voltage between the working electrode and the counter electrode are indicative of a malfunction, as for physiological reasons the analyte concentration in body tissues or the body liquid in the neighborhood of the sensor can change only relatively slowly. Very rapid variations may occur especially in the form of voltage peaks connected with poor contact conditions.

The reference electrode terminal and the counter electrode terminal of the potentiostat may be connected one to the other via a safety resistor. A faulty measurement of the differential potential between the working electrode and the counter electrode may lead to overdriving of the potentiostat and destruction of the electrodes. Such damage can be prevented by a high-resistance safety resistor between the reference electrode terminal and the counter electrode terminal. The safety resistor can have a resistance of at least 100 M ohms and can have a resistance of at least 1.0 G ohm.

In case such a safety resistor is used, the differential potential between the electric potentials of the counter electrode and the reference electrode is monitored as well. Malfunctions of the measuring system can be detected also by evaluation of that potential. For example, identity of the electric potentials of the counter electrode terminal and the reference electrode terminal is indicative of poor contact conditions of the reference electrode. The reference electrode terminal and the counter electrode terminal of the potentiostat can be connected one to the other via a safety resistor and where an evaluation unit monitors the difference of potential between the electric potentials of the counter electrode and the reference electrode in operation. While additional monitoring of the potential of the counter electrode is of advantage and allows malfunctions to be detected with higher reliability, some malfunctions can be detected already by monitoring the difference of potential between the counter electrode and the reference electrode alone.

However, use of such a safety resistor has a potential disadvantage that it may give rise to leakage currents. The risk of the electrodes being destroyed due to overdriving of the potentiostat can be avoided, without the use of a safety resistor, by an arrangement where the electric potential of the counter electrode is continuously monitored and the measuring system is switched off once the potential is found to lie outside the specified reference range.

A measuring system according to the invention comprises a testing resistor that permits a self-test to be carried out. By connecting the working electrode terminal of the potentiostat to the counter electrode terminal of the potentiostat via the testing resistor for testing purposes it is possible to apply a nominal voltage to the testing resistor and to compare the current flowing through the testing resistor with a nominal value obtained when the potentiostat is functioning properly. For carrying out such a self-test, the working electrode, the counter electrode, the reference electrode of the measuring system are preferably decoupled from the potentiostat by actuation of a switch that is connected in series with the respective terminal of the potentiostat.

Considering that a self-test carried out using the testing resistor allows malfunctions of the measuring system to be detected independently of the evaluation of the potential of the counter electrode, such a testing resistor constitutes an aspect of the present invention that may also have independent importance. The testing resistor can have at least one switch connected in series to the testing resistor, for connecting the working electrode terminal to the counter electrode terminal and can also be connected to the reference electrode terminal of the potentiostat via the testing resistor, for testing purposes.

BRIEF DESCRIPTION OF THE DRAWINGS

Further details and advantages of the invention will be explained hereafter by reference to one embodiment of the invention and to the attached drawing. In the drawings:

FIG. 1 shows a circuit diagram of a measuring system with malfunction detection embodiment.

DETAILED DESCRIPTION

FIG. 1 shows a first part of the measuring system, constituting the consumption component, consists of an implantable electrode system comprising a working electrode 1, a reference electrode 2 and a counter electrode 3. The electrodes 1, 2, 3 can be arranged on a common carrier, for example a plastic foil, intended for being inserted into a patient's body, for example into the subcutaneous fatty tissue.

The working electrode 1 carries an enzyme layer containing an enzyme that produces charge carriers by catalytic transformation of an analyte so that a current flowing between the working electrode 1 and the counter electrode 3 will be produced that correlates with the analyte concentration to be measured. For measuring the glucose concentration, a glucose oxidase may be used as an enzyme, for example.

The reference electrode 2 provides a reference potential for the working electrode 1, defined by a redox reaction, for example a silver/silver chloride reaction, taking place at the reference electrode.

The electrode system 1, 2, 3 is connected to a potentiostat 4 forming a second part of the measuring system. The potentiostat 4 comprises a working electrode terminal 15, to which the working electrode 1 is connected via a switch 13, a reference electrode terminal 19, to which the reference electrode 2 is connected via a switch 25, and a counter electrode terminal 16, to which the counter electrode 3 is connected via a switch 14.

In operation, the potentiostat 4 adjusts the electric potential between the working electrode 1 and the reference electrode 2 to a specified value so that no or only a negligible electric current flows through the reference electrode 2. The desired differential potential applied to the voltage input 6 of the potentiostat 4 is defined as $U_{cntr}$.

For controlling the electric potential between the working electrode 1 and the reference electrode 2, the reference electrode 2 is connected to the input of a follower stage 26 in the potentiostat 4. The output of the follower stage 26 is supplied to an input of an impedance transformer 27 whose output supplies the voltage of the counter electrode 3.

In the illustrated embodiment, the potentiostat 4 further detects the electric current flowing through the working electrode 1, i.e. between the counter electrode 3 and the working electrode 1, and generates, in combination with the current-to-voltage converter 7, a voltage signal $U_i$ proportional to the current measured, which is output at the voltage output 8 of the potentiostat 4. An evaluation unit 9, which has one input connected to that voltage output 8, evaluates the voltage signal $U_i$ for further determining therefrom the analyte concentration to be measured.

In the illustrated embodiment, the evaluation unit 9 is configured as a processor which simultaneously serves as control unit for the potentiostat 4. The control and evaluation unit 9 is capable of carrying out the complete evaluation of the voltage signal $U_i$, including the determination of the analyte concentration. In the illustrated embodiment, only a pre-evaluation or a data reduction step is carried out by the evaluation unit 9, which latter is carried on a patient's body together with the potentiostat 4. The final evaluation and calculation of concentration values is then carried out later by a separate unit 21, which communicates with the evaluation unit 9 wirelessly and which comprises a display 22 for displaying the analyte concentration values measured and further operating elements 23 for entering control commands.

A particularity of the illustrated embodiment is seen in the fact that the potential of the counter electrode 3 can be tapped via a voltage output 10 of the potentiostat 4. The working electrode 1 being connected to mass in the illustrated embodiment, the electric potential measured at the counter electrode 3 corresponds to the electric voltage between the working electrode 1 and the counter electrode 3.

In operation, the evaluation unit 9 monitors the electric potential $U_{CE}$ of the counter electrode 3 via the voltage output 10 of the potentiostat 4 and generates a malfunction signal when that potential $U_{CE}$ comes to lie outside the specified reference range, for example when it deviates from a reference value by more than the threshold value. The malfunction signal may be transmitted to a user as a visual or an acoustic warning signal, for example. There is, however, also the possibility that the malfunction signal may cause the system to be switched off in order to prevent consequential damage. It may be provided that in such a case the system will be switched on automatically after a specified period of time of, for example, 1 to 5 minutes, because temporary malfunctions may be caused, for example, by an inadequate exchange of liquids in the environment of the implanted electrodes 1, 2, 3, and may under certain circumstances be remedied automatically by the patient's movements. There is, however, also the possibility to continue operation of the measuring system initially when a malfunction signal is encountered, and simply to classify as unreliable those measuring results that are obtained after occurrence of the malfunction signal. In that case, it would be favorable to specify a threshold value and to set up the evaluation unit 9 in a manner such that the measuring system will be switched off when the potential $U_{CE}$ of the counter electrode 3 deviates from the reference range by more than the threshold value. The malfunction signal may be transmitted to the indicator unit 22 by radio, for example.

The potential values to be expected during trouble-free operation depend on the type of sensor used, for example on the size of the electrode surfaces and the conditions of the electrochemical reaction by which charge carriers are produced at the working electrode 1. The reference range may be preset for a given electrode system. Preferably, the reference range is defined as a function of the current flow between the working electrode 1 and the counter electrode 3. In that case, the reference range may be calculated by the evaluation unit 8 from the value of the electric current measured at any time, based on a specified formula, or may be taken from a pre-stored table.

In the case of the described embodiment, a first reference range is specified as a function of the current flowing between the working electrode 1 and the counter electrode 3. To permit even short-time temporary disturbances to be detected, an additional second reference range is defined the limits of which are a function of a former value of the electric voltage between the working electrode 1 and the counter electrode 3.

Given the fact that analyte concentrations vary in a human body relatively slowly, as a rule over a period of some minutes or hours, any abrupt changes, occurring for example within less than 30 seconds, are also to be taken as an indication of a malfunction. A reference range which is a function of a former value of the electric potential of the counter electrode 3 allows such disturbances to be detected more rapidly. In the simplest case, a specified value or an average of a specified number of former values may be used as a reference value, and a related threshold value may be specified as an absolute value in order to define the reference range within which potential values, for example, that deviate from the reference value by more than the threshold value, are defined as lying outside the reference range.

The speed with which analyte concentrations vary in a human body, naturally depends on the respective analyte, for example glucose or lactate, so that no generally valid values can be specified. However, a suitable reference range normally can be found for an analyte concentration, at least by trial, for example by determining a threshold value for a reference value, that may be a function of preceding values, and by specifying that value as an absolute value, especially when it is the aim to classify voltage peaks caused by poor contact conditions as faulty conditions.

Generally, malfunctions of the described measuring system may be caused by the electrodes 1, 2, 3 by poor contact conditions, or even by interrupted leads, or else by a defect of the potentiostat 4. In order to be able to locate the cause of any detected malfunction more precisely, the illustrated embodiment comprises a testing resistor 12 for performing a self-test.

One end of the testing resistor 12 is connected to a switch 13, 14, 25. Using the switches 13, 14 the testing resistor 12 can connect the working electrode terminal 15 to the counter electrode terminal 16 of the potentiostat 4 for testing purposes. Further, the reference electrode terminal 19 can be connected to the potential of the counter electrode terminal 16 via the switch 25.

For performing a self-test of the measuring system, the working electrode 1, the reference electrode 2 and the counter electrode 3 are decoupled from the respective terminals 15, 16, 19 of the potentiostat 4 via switches 13, 14 and 25, respectively. When a known voltage, for example the nominal voltage $U_{cntr}$ of the differential potential between the reference electrode 2 and the working electrode 1 is then connected to the counter electrode terminal 16 via the switch 17, the current flowing through the testing resistor 12 is measured by the system instead of the current normally flowing between the counter electrode 3 and the working electrode 1. When the resistance of the testing resistor 12 is known, the current so measured can be compared with an expected current, and when considerable deviations exist this can be taken as an indication of a malfunction of the potentiostat 4.

Preferably, the evaluation unit 9 is set up so that the self-test described before will be carried out automatically when a malfunction signal is generated as a result of a suspicious potential between the working electrode 1 and the counter electrode 3, or between the reference electrode 2 and the counter electrode 3. In case a malfunction of the potentiostat 4 is detected during that self-test, this may be indicated to a user by an alarm signal, for example an acoustic signal, so that the potentiostat 4 can be exchanged. If no malfunction of the potentiostat 4 is detected it can be assumed that the malfunction had been caused by the electrodes 1, 2, 3 or their implantation environment, respectively. As the implantation environment reacts sensitively to any movement of the patient, any malfunctions caused in this way will frequently disappear all by themselves so that the user needs to be informed of malfunctions resulting from the electrode system 1, 2, 3 only when they persist for an extended period of time.

If no malfunction of the potentiostat 4 is detected during a self-test performed by the testing resistor 12, then the described measuring system will perform another self-test in which the counter electrode 3 is decoupled from the counter electrode terminal 16 of the potentiostat 4 by actuation of the switch 14, while the working electrode 1 and the reference electrode 2 are coupled to the respective terminals of the potentiostat 4. In that case, no notable current will flow through the electrode system 1, 2, 3. With the result that the electric potential present at the working electrode 1 will change due to the electrochemical processes taking place at that point, tending to reach a new equilibrium.

The electric potential present at the working electrode 1 under no-current conditions may be described as open-circuit potential. The electric potential $U_{pot}$ of the working electrode 1 is output by the potentiostat 4 at its voltage output 18, and is likewise tested by the evaluation unit 8 to detect any irregularities. When the open-circuit potential deviates from a nominal value by more than a specified threshold value, this is taken as an indication of a malfunction of the working electrode 1 and/or of the potentiostat 4. Significantly increased values are frequently due to changed conditions of the surfaces of the working electrode or of the reference electrode. Extremely high values are indicative of contact problems.

In a potentiostat 4, faulty measurements of the differential potential between the working electrode 1 and the reference electrode 2 that may by due, for example, to poor contact conditions of the reference electrode 2 or the working electrode 1, may cause the potentiostat 4 to overdrive and to cause damage, especially to destroy the electrodes. This can be prevented by connecting the reference electrode terminal 19 to the counter electrode terminal 16 via a safety resistor 24. Preferably, the safety resistor 24 has a resistance value of at least 100 Mohms, preferably least one Gohm.

Thus, embodiments of the in vivo monitor with malfunction detection are disclosed. One skilled in the art will appreciate that the teachings can be practiced with embodiments other than those disclosed. The disclosed embodiments are presented for purposes of illustration and not limitation, and the invention is only limited by the claims that follow.

What is claimed is:

1. Measuring system for in vivo monitoring of an analyte concentration with malfunction detection, comprising:
    an electrode system comprising,
        a working electrode,
        a reference electrode, and
        a counter electrode;
    a potentiostat for adjusting a difference of potential between the electric potential of the working electrode and the electric potential of the reference electrode to a specified value and for measuring an electric current flowing between the working electrode and the counter electrode, the potentiostat comprising,
    a working electrode terminal for connection to the working electrode,
    a reference electrode terminal for connection to the reference electrode, and
    a counter electrode terminal for connection to the counter electrode;
    an evaluation unit which monitors the electric potential of the counter electrode and which generates a malfunction signal when said potential is outside a specified reference range.

2. The measuring system in claim 1 wherein the reference range is specified as a function of the current flowing between the working electrode and the counter electrode.

3. The measuring system in claim 1 wherein the reference range is specified as a function of a number of former values of the electric potential of the counter electrode.

4. The measuring system as in claim 1 further comprising, a safety resistor connected between the reference electrode terminal and the counter electrode terminal.

5. The measuring system in claim 1 further comprising, a switch for decoupling the counter electrode from the counter electrode terminal of the potentiostat.

6. The measuring system in claim 1 further comprising, a switch for decoupling the working electrode from the working electrode terminal of the potentiostat.

7. The measuring system in claim 1 further comprising, a testing resistor and at least one switch connected in series with the testing resistor for connecting the working electrode terminal to the counter electrode terminal of the potentiostat via the testing resistor for testing purposes.

8. The measuring system in claim 7 further comprising, a testing switch for supplying a nominal potential to the counter electrode terminal of the potentiostat for testing purposes.

9. The measuring system in claim 1 further comprising, a display for displaying measured analyte concentration values, wherein the evaluation unit communicates with the display wirelessly for transmitting to the display the malfunction signal which is produced when the electric voltage between the working electrode and the counter electrode deviates from the reference value by more than the threshold value.

10. A method for detecting malfunctions of a measuring system for in vivo measurement of an analyte concentration, comprising
    measuring an electric current flowing between a working electrode and a counter electrode the intensity of which correlates with the analyte concentration to be measured;
    monitoring an electric potential of the counter electrode;
    decoupling the counter electrode from the potentiostat;
    measuring the electric potential then occurring at the working electrode; and,
    detecting malfunctions upon any deviation of the measured potential from a threshold value and the existence of a malfunction is derived when the deviation exceeds a specified threshold value.

11. Measuring system for in vivo monitoring of an analyte concentration with malfunction detection, comprising:
    an electrode system comprising,
        a working electrode,
        a reference electrode, and
        a counter electrode;
    a potentiostat for adjusting a difference of potential between the electric potential of the working electrode and the electric potential of the reference electrode to a specified value and for measuring an electric current flowing between the working electrode and the counter electrode, the potentiostat comprising,
        a working electrode terminal for connection to the working electrode,
        a reference electrode terminal for connection to the reference electrode, and
        a counter electrode terminal for connection to the counter electrode;
    a testing resistor and at least one switch connected in series with the testing resistor for connecting the working electrode terminal to the counter electrode terminal of the potentiostat via the testing resistor for testing purposes;
    a testing switch for supplying a nominal potential to the counter electrode terminal of the potentiostat for testing purposes; and,
    an evaluation unit which monitors the electric potential of the counter electrode and which generates a malfunction signal when said potential is outside a specified reference range.

12. Measuring system for in vivo monitoring of an analyte concentration with malfunction detection, comprising:
    an electrode system comprising,
        a working electrode,
        a reference electrode, and
        a counter electrode;
    a potentiostat for adjusting a difference of potential between the electric potential of the working electrode and the electric potential of the reference electrode to a specified value and for measuring an electric current flowing between the working electrode and the counter electrode, the potentiostat comprising,
        a working electrode terminal for connection to the working electrode,
        a reference electrode terminal for connection to the reference electrode, and
        a counter electrode terminal for connection to the counter electrode;
    a testing switch for supplying a nominal potential to the counter electrode terminal of the potentiostat for testing purposes; and, an evaluation unit to monitor the electric potential of the counter electrode and which generates a malfunction signal when said potential is outside a specified reference range.

13. The method of claim 10 wherein the step of measuring the electric potential then occurring at the working electrode comprises measuring an open circuit potential.

* * * * *